(12) United States Patent
Cheng et al.

(10) Patent No.: US 9,109,218 B2
(45) Date of Patent: Aug. 18, 2015

(54) HUMAN ARGINASE AND PEGYLATED HUMAN ARGINASE AND THE USE THEREOF

(71) Applicant: BIO-CANCER TREATMENT INTERNATIONAL LTD. (SHANGHAI), Shanghai (CN)

(72) Inventors: Ning Man Cheng, Hong Kong (HK); Li Chen, Hong Kong (HK)

(73) Assignee: Bio-Cancer Treatment International Ltd. (Shanghai), Shanghai (CN)

( * ) Notice: Subject to any disclaimer, the term of this patent is extended or adjusted under 35 U.S.C. 154(b) by 0 days.

(21) Appl. No.: 14/368,507

(22) PCT Filed: Dec. 23, 2012

(86) PCT No.: PCT/CN2012/087241
§ 371 (c)(1),
(2) Date: Jun. 25, 2014

(87) PCT Pub. No.: WO2013/097658
PCT Pub. Date: Jul. 4, 2013

(65) Prior Publication Data
US 2014/0363417 A1    Dec. 11, 2014

(30) Foreign Application Priority Data

Dec. 27, 2011 (CN) .......................... 2011 1 0445965
Mar. 16, 2012 (CN) .......................... 2012 1 0069626

(51) Int. Cl.
*C12N 9/78* (2006.01)
*A61K 38/50* (2006.01)
*C12N 9/96* (2006.01)

(52) U.S. Cl.
CPC . *C12N 9/78* (2013.01); *A61K 38/50* (2013.01); *C12N 9/96* (2013.01); *C12Y 305/03001* (2013.01)

(58) Field of Classification Search
CPC .................................. C12N 9/80; C12N 9/96
USPC .......................... 435/183; 530/350; 514/12.1
See application file for complete search history.

(56) References Cited

U.S. PATENT DOCUMENTS 8,507,245 B2    8/2013 Leung et al.
2005/0244398 A1* 11/2005 Cheng et al. ................. 424/94.4

FOREIGN PATENT DOCUMENTS

| CN | 1345966 | 4/2002 |
| CN | 1745847 | 3/2006 |
| WO | 2010124547 | 11/2010 |
| WO | 2011008495 | 1/2011 |

OTHER PUBLICATIONS

Arginase-1 isoform 2 [*Homo sapiens*], Database GenBank [online], May 2014, Accession No. NP_000036.2.
Arginase [EC 3.5.3.1], [*Homo sapiens*], Database GenBank [online], Oct. 31, 1994, Accession No. AAA51776.1.
Wang, Yinghua et al., Mutation of Arginines Near the Active Site Cys 124 of Human Dual-specificity Phosphatase and Its Effect on the Enzymatic Activity, Acta Biochimica Et Biophysica Sinica, Dec. 31, 2003, pp. 149-153, vol. 35, No. 2, ISSN: 0582-9879.
Alarco'N, R. et al., Mutational analysis of substrate recognition by human arginase type I-agmatinase activity of the N130D variant, FEBS Journal, Dec. 31, 2006, pp. 5625-5631, vol. 273, ISSN: 1742-464X.
Lakshmi Santhanam et al., Inducible NO Synthase-Dependent S-Nitrosylation and Activation of Arginase1 Contribute to Age-Related Endothelial Dysfunction, Circulation Research, Aug. 17, 2007, pp. 692-702, 101(7).
*Homo sapiens* arginase, liver, mRNA (cDNA clone MGC:22316 Image:4712189), complete cds, Database GenBank [online], Jul. 15, 2006, Accession No. BC020653.

* cited by examiner

*Primary Examiner* — Maryam Monshipouri
(74) *Attorney, Agent, or Firm* — Eagle IP Limited; Jacqueline C. Lui

(57) ABSTRACT

The present invention provides a site-directed mutated arginase and the preparation method thereof, and the use of said site-directed mutated arginase in preparing a medicament for treating an arginase-related disease. The present invention also provides a pegylated arginase and the preparation method thereof, and the use of said pegylated arginase in preparing a medicament for treating an arginase-related disease.

23 Claims, 6 Drawing Sheets

```
atgagcgcca agtccagaac catagggatt attggagctc ctttctcaaa ggacagcca      60
cgaggaggg  tggaagaagg ccctacagta ttgagaaagg ctggctgct  tgagaaactt    120
aaagaacaag agtgtgatgt gaaggattat gggacctgc  cctttgctga catccctaat    180
gacagtcct  ttcaaattgt gaagaatcca aggtctgtgg aaaagcaag  cgagcagctg    240
gctggcaagg tggcagaagt caagaagaac ggaagaatca gctggtgct  gggagagac     300
cacagtttgg caattggaag catctctggc catgccaggg tccaccctga tcttggagtc    360
atctgggtgg atgctcacac tgatatcaac actccactga caaccacaag tggaaacttg    420
catggacaac ctgtatcttt cctcctgaag gaactaaaag gaaagattcc cgatgtgcca    480
ggattctcct gggtgactcc ctgtatatct gccaaggata ttgtgtatat tggcttgaga    540
gacgtggacc ctggggaaca ctacattttg aaaactctag gcattaaata cttttcaatg    600
actgaagtgg acagactagg aattggcaag gtgatggaag aaacactcag ctatctacta    660
ggaagaaaga aaggccaat  tcatctaagt tttgatgttg acggactgga cccatctttc    720
acaccagcta ctggcacacc agtcgtggga ggtctgacat acagagaagg tctctacatc    780
acagaagaaa tctacaaaac agggctactc tcaggattag atataatgga agtgaaccca    840
tccctgggga agacaccaga agaagtaact cgaacagtga acacagcagt tgcaataacc    900
ttggcttctt tcggacttgc tcaggaggt  aatcacaagc ctattgacta ccttaaccca    960
cctaagtaa                                                            969
```

Fig 1

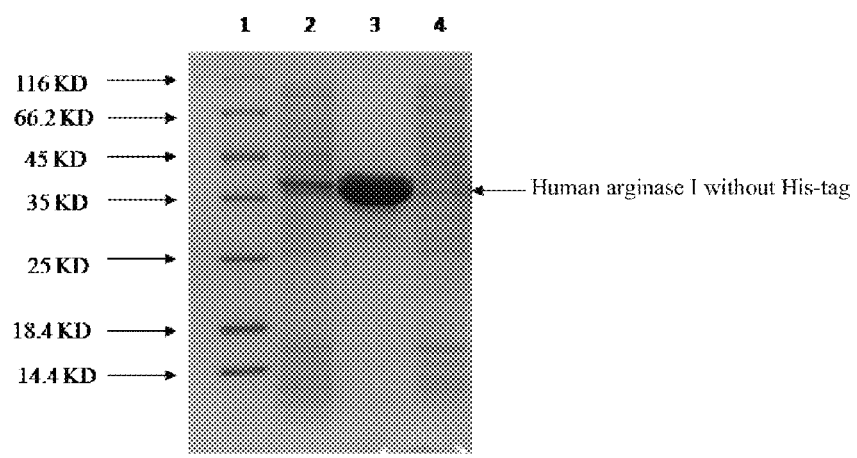

Fig 2

Area Percentage Report

| Sort | : | Signal |
|---|---|---|
| Multiplier | : | 1.0000 |
| Dilution | : | 1.0000 |
| Sample Amount | : | 20.00000 [ng/ul] (Not used in calibration) |

ISTD use multiplier and dilution

Signal 1: VWD1 A, wavelength = 280 nm

| Peak # | Retention Time [min] | Type | Peak Width [min] | Peak Area mAU*s | Peak Height [mAU] | Peak Area % |
|---|---|---|---|---|---|---|
| 1 | 7.076 | BB | 1.0143 | 1267.44189 | 17.13606 | 95.5066 |
| 2 | 10.041 | MM R | 0.7370 | 59.63036 | 1.34852 | 4.4934 |
| Total: | | | | 1327.07226 | 18.48458 | |

SEQUENCE LISTING

```
<160> NUMBER OF SEQ ID NOS: 2

<210> SEQ ID NO 1
<211> LENGTH: 322
<212> TYPE: PRT
<213> ORGANISM: Homo sapiens

<400> SEQUENCE: 1

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285
```

-continued

```
Val Thr Arg Thr Val Asn Thr Ala Val Ala Ile Thr Leu Ala Cys Phe
    290                 295                 300
Gly Leu Ala Arg Glu Gly Asn His Lys Pro Ile Asp Tyr Leu Asn Pro
305                 310                 315                 320
Pro Lys

<210> SEQ ID NO 2
<211> LENGTH: 969
<212> TYPE: DNA
<213> ORGANISM: Homo sapiens

<400> SEQUENCE: 2
atgagcgcca agtccagaac catagggatt attggagctc ctttctcaaa gggacagcca       60
cgaggagggg tggaagaagg ccctacagta ttgagaaagg ctggtctgct tgagaaactt      120
aaagaacaag agtgtgatgt gaaggattat ggggacctgc cctttgctga catccctaat      180
gacagtccct ttcaaattgt gaagaatcca aggtctgtgg aaaagcaag cgagcagctg       240 gctggcaagg tggcagaagt caagaagaac ggaagaatca gcctggtgct gggcggagac      300
cacagtttgg caattggaag catctctggc catgccaggg tccaccctga tcttggagtc      360
atctgggtgg atgctcacac tgatatcaac actccactga caaccacaag tggaaacttg      420
catggacaac ctgtatcttt cctcctgaag gaactaaaag gaaagattcc cgatgtgcca      480
ggattctcct gggtgactcc ctgtatatct gccaaggata ttgtgtatat tggcttgaga      540
gacgtggacc ctggggaaca ctacattttg aaaactctag gcattaaata cttttcaatg      600
actgaagtgg acagactagg aattggcaag gtgatggaag aaacactcag ctatctacta      660
ggaagaaaga aaaggccaat tcatctaagt tttgatgttg acggactgga cccatctttc      720
acaccagcta ctggcacacc agtcgtggga ggtctgacat acagagaagg tctctacatc      780
acagaagaaa tctacaaaac agggctactc tcaggattag atataatgga agtgaaccca      840
tccctgggga agacaccaga agaagtaact cgaacagtga acacagcagt tgcaataacc      900
ttggcttgtt tcggacttgc tcgggagggt aatcacaagc ctattgacta ccttaaccca      960
cctaagtaa                                                              969
```

HUMAN ARGINASE AND PEGYLATED HUMAN ARGINASE AND THE USE THEREOF

This application claims priorities from the Chinese Patent Application No. 201110445965.8, filed on Dec. 27, 2011, entitled "Human arginase and pegylated human arginase and the use thereof", and from the Chinese Patent Application No. 201210069626.9, filed on Mar. 16, 2012, entitled "Human arginase and pegylated human arginase and the use thereof", which are incorporated herein by reference in their entirety.

REFERENCE TO SEQUENCE LISTING

The hard copy of the sequence listing submitted herewith and the corresponding computer readable form are both incorporated herein by reference in their entireties.

FIELD OF INVENTION

The present invention provides an arginase, the preparation method thereof and the use thereof in the treatment of arginase-related diseases. Specifically, the present invention provides a site-directed mutated arginase, the preparation method thereof and the use thereof in the treatment of arginase-related diseases. The present invention also provides a pegylated arginase, the preparation method thereof and the use thereof.

BACKGROUND OF THE INVENTION

Arginine is an important amino acid in mammals including human, which is involved in various physiological processes, including cell proliferation and growth. For example, arginine is an immediate precursor for the synthesis of the potential signal molecule nitric oxide (NO). NO functions as a neurotransmitter, a muscle relaxant or a vasodilator. The biosynthesis of NO involves nitric oxide synthase catalyzed $Ca^{++}$ and NADPH-dependent reactions. Another function of arginine is as a precursor for polyamine, spermidine or spermine and participates in different physiological processes.

Studies showed that when arginine is less than 8 µM, cancer cells undergo irreversible death (Srorr & Burton, 1974, The effects of arginine deficiency on lymphoma cells. Br. J. Cancer 30, 50). By studying the effect on cell growth, it was found that upon removal of arginine, the normal cells in the cell cycle G0 phase would enter a resting state and remain viable for several weeks without significant damage; when the concentration of arginine returned to normal level, the cells would return to normal cell cycle. However certain tumor cells would proceed from the 'R' point of the cell cycle G1 phase to S phase at deprivation of arginine, and undergo apoptosis soon. The apoptosis of tumor cells as a result of arginine deficiency is irreversible. Therefore, scientists began to consider treating cancers by controlling the level of arginine in the body, especially for auxotrophic tumors such as liver cancer and melanoma. This approach has now been used to study the inhibition of various tumors, including breast cancer, small cell lung cancer, prostate cancer, lymphoma and leukemia.

Arginase is the enzyme catalyzing the hydrolysis of L-arginine into ornithine and urea. In general, arginase is expressed in liver, kidney and testis of the urea-producing animals (mammals, elasmobranchs, amphibians, and turtles) as one of the enzymes of the urea cycle. Arginase catalyzes the final step of the urea recycle pathway in mammals, converting arginine to ornithine and urea. In most mammals including human, the family of arginase includes arginase I and arginase II. Arginase I is mainly expressed in the liver cells, and arginase II is mainly expressed in the kidney and erythrocytes.

There are two methods to produce arginase; of which one is to separate it from the arginase producing organism, and the other is through recombinant genetic engineering techniques. The latter has its advantages. For example, experiments have showed that a great amount of arginase could be produced by E. coli. However, there may be technical problems to produce arginase through recombinant genetic engineering techniques, such as low enzyme activity or poor stability and short half-life in vivo, limiting its application in clinical practice.

U.S. Pat. No. 7,951,366B2 disclosed a pharmaceutical composition and method for the treatment of human malignant tumor by arginine depletion using recombinant human arginase I with his-tag, wherein the arginase is modified by covalently conjugated with polyethylene glycol of molecular weight of 5,000 (MW5, 000) at the N-terminal or the amine group on the surface of the arginase. The modified human arginase had an increased stability with a half-life of 3 days in human serum.

US20100247508A1 disclosed a modified human arginase with his-tag, wherein the 168 and 303 cysteines are replaced with serines and the arginase is pegylated with polyethylene glycol of a molecular weight of 20 KDa. Like the recombinant human arginase I disclosed in U.S. Pat. No. 7,951,366B2, an additional peptide fragment, His-tag is included in the amino acid sequence of the arginase. The drug regulatory agencies in most countries do not recommend the use of these peptide fragments. For example, China State Food and Drug Administration indicates in the "Technical Quidelines on the Quality Control of Recombinant DNA Product for Human Use" that additional peptide fragments such as His-tag introduced for the purpose of simplifying the production process should be removed as far as possible from the final product.

WO 2011/008495A2 disclosed a site-directed modified arginase, in which the three cysteines were retained and another cysteine residue is introduced substituting the third amino acid residue of the N-terminus, and then pegylated with methoxy polyethylene glycol maleimide of molecular weight of 20 KDa. Since the said human arginase still carries the original three cysteine residues, its pegylation product is prone to heterogeneous and low in yield, which also adds difficulties for purification.

The present technical field has the need for a better arginase or derivatives thereof, for the treatment of arginine related diseases or disorders.

SUMMARY OF THE INVENTION

The present invention provides an isolated and substantially pure arginase. Arginase is the enzyme in the final step of the urea recycle pathway in the synthesis of urea in mammals, converting arginine to ornithine and urea. In most mammals including human, the family of arginase includes arginase I and arginase II. Studies on arginase I of various origins showed that arginase I of different origins have a lot of conserved regions and active sites, though their sequence may be different. As reported by Haraguchi, Y., etc., 1987, Proc. Natl. Acad. Scl. 84, 412-415, wild-type human arginase I has an amino acid sequence of SEQ ID NO.1, which comprises three cysteines at amino acid position 45, 168 and 303. The wild-type human arginase I has a nucleic acid sequence of SEQ ID NO. 2.

In the present invention, the term "isolated" refers to a non-natural form. The term "substantial pure" means that the product may comprise other components derived from production or protein modification, yet such other components are substantially not present or only present in a small ratio.

In the present invention, the description on the location of amino acid site is commonly used by the skilled in the art. For example, the phrase "in position 45 of the sequence of SEQ ID NO.x" or "Cys (cysteine) in position 45 of the sequence of SEQ ID NO.x" or "Cys45" all refers to the 45$^{th}$ amino acid residue in the amino sequence or the cysteine in position 45.

In one aspect, the present invention provides a mutant arginase, which is a human arginase I comprising
(1) an amino acid sequence of SEQ ID NO:1, wherein any one, two or three of the cysteines at positions 45, 168 and 303 is/are mutated, or
(2) an amino acid sequence wherein substitution, deletion, insertion, addition or inversion of one or more amino acids is introduced in the amino acid sequence defined in (1),
and which has arginase activity.

In one aspect, the cysteines in the arginase of the present invention are independently mutated to non-polar amino acids. According to the properties of their side chain, the amino acids can be classified as polar or non-polar amino acids. Amino acids having side chains being uncharged or weakly polarized are called non-polar amino acids, such as, glycine, alanine, valine, leucine, isoleucine, methionine, phenylalanine, tryptophan and proline.

In one aspect, the cysteines in the arginase of the present invention are independently mutated to glycine, alanine, valine, leucine, isoleucine, methionine, phenylalanine, tryptophan or proline. Preferably, the cysteines are independently mutated to alanine. The present invention has unexpectedly found that the enzymatic activity of human arginase I is significantly increased when the cysteine, which is a non-ionic polar amino acid is mutated to a non-polar amino acid (such as alanine). One of the possible reasons is the binding between the mutant arginase and the substrate is enhanced.

In one aspect, one of the cysteines at positions 45, 168 and 303 of the arginase of the present invention is mutated. In a further aspect of the present invention, cysteine at position 303 is mutated. Preferably, said cysteine is mutated to glycine, alanine, valine, leucine, isoleucine, methionine, phenylalanine, tryptophan or proline; and more preferably, said cysteine is mutated to alanine.

In one aspect, any two of the cysteines at positions 45, 168 and 303 of the arginase of the present invention are mutated. In a further aspect of the present invention, cysteines at positions 45 and 303 are mutated. Preferably, said cysteines are mutated to glycine, alanine, valine, leucine, isoleucine, methionine, phenylalanine, tryptophan or proline; and more preferably, said cysteines are mutated to alanine.

In one aspect, the cysteines at positions 168 and 303 of the amino acid sequence of SEQ ID NO. 1 in the arginase of the present invention are mutated. Preferably, said cysteines are mutated to glycine, alanine, valine, leucine, isoleucine, methionine, phenylalanine, tryptophan or proline; and more preferably, said cysteines are mutated to alanine.

In one aspect, the cysteines at positions 45 and 303 of the amino acid sequence of SEQ ID NO. 1 in the argianse of the present invention are mutated. Preferably, said cysteines are mutated to glycine, alanine, valine, leucine, isoleucine, methionine, phenylalanine, tryptophan or proline; and more preferably, said cysteines are mutated to alanine.

In one aspect, the cysteines at positions 45, 168 and 303 of the amino acid sequence of SEQ ID NO. 1 in the arginase of the present invention are mutated. Preferably, said cysteines are mutated to glycine, alanine, valine, leucine, isoleucine, methionine, phenylalanine, tryptophan or proline; and more preferably, said cysteines are mutated to alanine.

The arginase of the present invention has higher enzymatic activity than the wild-type arginase. The arginase of present invention generally has a specific activity of at least about 500 U/mg; preferably, the activity is at least about 700 U/mg; and more preferably, the activity is at least about 800 U/mg. Arginase of the present invention generally has higher enzymatic activity than the wild-type arginase.

In one aspect of the present invention, the arginase has a nucleotide sequence of SEQ ID NO. 2, wherein at least one codon for amino acid residue cysteine at position 45, 168 and 303 of the amino acid sequence of SEQ ID NO.1 is substituted. Amino acids are encoded by polynucleotides. A three-nucleotide codon in a messenger RNA defines a single amino acid. In one aspect of the present invention, the nucleotide substitution is the codon TGT substituted by a codon encoding for glycine, alanine, valine, leucine, isoleucine, methionine, phenylalanine, tryptophan or proline. Preferably, the codon TGT is substituted by a codon encoding for alanine.

In one aspect of the present invention, said codons encoding for alanine is GCT, GCC, GCA, GCG, and preferably is GCT.

In one aspect, the present invention provides a method for preparing the arginase mentioned above, including expressing the gene of the arginase or mutant arginase in a host which is able to express the protein. The preparation method for the arginase of present invention generally includes the following major steps. Desired genes or nucleotide fragments are obtained by PCR or synthetic method. The DNA fragment with the desired gene is linked with a vector, such as a plasmid, phage or virus, which can replicate independently and has a selection marker to form recombinant DNA molecules. The ligation of DNA fragments into a vector is mainly through homopolymer tails, cohesive ends, blunt-end or artificial linker. Recombinant DNA has to be introduced into the host cell in order to be multiplied and expressed. According to the different properties of the vectors, transfection, transformation, transduction are carried out so that the recombinant DNA molecules are introduced into a host cell and multiplied. Suitable genetic engineering hosts are well known in the art, which include *Escherichia coli*, yeast, insect cells and the like.

The present invention also provides an isolated and substantially pure pegylated arginase. The arginase in the said pegylated arginase is as previously defined. In one aspect, one, two or three of the cysteines at positions 45,168 and 303 of said arginase of the present invention in the amino sequence of SEQ ID NO.1 is/are mutated; preferably, said cysteine(s) is/are mutated to non-polar amino acids; more preferably, said cysteine(s) is/are mutated to alanine, glycine, valine, leucine, isoleucine, methionine, phenylalanine, tryptophan, or proline; and most preferably, said cysteine(s) is/are mutated to alanine. The pegylated arginase of the present invention is obtained by pegylation of said arginase. In said pegylated arginase, polyethylene glycol molecule is covalently linked with the amino acid residues of the arginase. In the present invention, each of the arginase is linked with at least one polyethylene glycol molecule to form the pegylated arginase.

In one aspect, the present invention provides a pegylated arginase, wherein the arginase is a human arginase I which comprises (1) an amino acid sequence of SEQ ID NO:1, wherein any one, two or three of cysteines at positions 45, 168 and 303 is/are mutated, or (2) an amino acid sequence wherein substitution, deletion, insertion, addition or inversion of one or more amino acids is introduced in the amino acid sequence defined in (1), and which has arginase activity.

In one aspect, the cysteines in the pegylated arginase of the present invention are independently mutated to non-polar amino acid. The structures of the 20 amino acids are different due to the difference of their side chain. Amino acids having side groups being uncharged or weakly polarized belong to non-polar amino acids, such as, glycine, alanine, valine, leucine, isoleucine, methionine, phenylalanine, tryptophan and proline.

In one aspect of the invention, the pegylated arginase I does not comprise a tag sequence for use in the purification, such as a His-tag sequence added at the C or N terminus. His-tag fusion protein is the most common means of protein expression, which has the advantage of easy for purification and without significant effect to the activity of the protein. Protein expression products either in soluble form or in inclusion body could be purified by immobilized metal ion affinity chromatography. On the other hand, because of the potential immunogenicity property, China State Food and Drug Administration indicates in the "Technical Quidelines on the Quality Control of Recombinant DNA Product for Human Use" that additional peptide fragments such as His-tag introduced for the purpose of simplifying the production process should be removed as far as possible from the final product.

In the present invention, the pegylation of the arginase can be achieved by chemical modification, wherein said chemical modification can be carried out by covalently conjugate a polyethylene glycol molecule with arginase using a polyethylene glycol derivative with a coupling agent (also referred to as a pegylation reagent). Common polyethylene glycol molecule has a hydroxyl group at each end thereof. A methoxy polyethylene glycol (mPEG) is a polyethylene glycol blocked in one end with a methoxy group. The most commonly studied pegylation reagents used in the modification of peptides or proteins are derivatives of methoxy polyethylene glycol (mPEG). The modification mainly includes that to the amino group, carboxyl group or the thiol group. One of the common pegylation method is to covalently link polyethylene glycols or pegylation reagents with $\epsilon$-$NH_2$ of surface lysine or N-termial $\alpha$-$NH_2$ of the protein, such as methoxy polyethylene glycol-succinimidyl butyrate (mPEG-SBA), mPEG-succinimidyl propionate (mPEG-SPA), mPEG-succinimidyl succinate (mPEG-SS), mPEG-succinimidyl carbonate (mPEG-SC), mPEG-Succinimidyl Glutarate (mPEG-SG), mPEG-N-hydroxy-succinimide (mPEG-NHS), mPEG-tresylate and mPEG-aldehyde. Due to the high nucleophile property of thiol group, another commom pegylation method is the selective use of polyethylene glycols or pegylation reagents which can specifically conjugated with the thiol group of proteins, such as mPEG-maleimide, mPEG-ortho-pyridyl-disulphide, mPEG-vinylsulfone and mPEG-iodoacetamide to modify the thiol group of peptides or proteins. Human arginase has three cysteine residues located at positions 45, 168 or 303 of the amino acid sequence, which can be site-directed modified by covalently conjugated with the PEG molecules targeting at thiol group.

The amino acid sequence of the arginase I of the present invention comprises 24 lysines and N-terminal amino group as potential sites for amino group pegylation; each has different degree of pgylation due to the different location in the 3-dimentional structure of the protein. From 3-dimentional structure analysis of arginase by PyMOL or Swiss-Pdb-Viewer, 12 out of 24$\epsilon$-amino groups are difficult to be pegylated due to the steric hindrance or the hydrogen bonds formed with the surrounding groups. $\epsilon$-amino groups of K4, K33, K41, K75, K89, K150, K155, K191, K224, K284, K313, and K322 are accessible for reactions by PEG reagents targeting at amino group, and $\epsilon$-amino groups of K191, K224, K89, K284 are the easiest accessible sites for pegylation In one aspect of the present invention, said pegylation reagent is selected from methoxy polyethylene glycol-succinimidyl propionate (mPEG-SPA), mPEG-succinimidyl butyrate (mPEG-SBA), mPEG-succinimidyl succinate (mPEG-SS), mPEG-succinimidyl carbonate (mPEG-SC), mPEG-Succinimidyl Glutarate (mPEG-SG), mPEG-N-hydroxyl-succinimide (mPEG-NHS), mPEG-tresylate and mPEG-aldehyde. In a further aspect of the present invention, said pegylation reagent is methoxy polyethylene glycol-succinimidyl propionate; preferably said pegylation reagent is methoxy polyethylene glycol-succinimidyl propionate 5000 with an average molecular weight of 5K.

The selection of molecular weight of the PEG should make a comprehensive consideration of the bio-activity and the pharmacokinetics properties. Studies showed that the acting time of the modified protein drugs in the body is correlated with the numbers and molecule weight of PEG conjugated. Proteins modified with too large PEG molecules may lose some of their activity. The PEG used for the present invention has a molecule weight ranging from 5K to 40K, linear or branched. The PEG used for the present invention can be PEG derivatives used in the technical field. The PEG used for the present invention is not limited to certain specified types.

In one aspect of the present invention, the total molecular weight of PEG molecules conjugated with each molecule of said arginase is about 20-70K; and preferably, the total molecular weight is about 30-60K.

In one aspect of the present invention, each of the PEG molecule used in the pegylation has an average molecular weight of about 2-40K; preferably, average molecular weight is about 5-20K; and more preferably, average molecular weight is about 5K.

In one aspect of the present invention, each of the PEG molecule used in pegylation has an average molecular weight of about 5K; and each arginase molecule is conjugated with about 4-13 PEG molecules; and preferably, each arginase molecule is conjugated with 6-12 PEG molecules.

The number of PEG molecules conjugated with each molecule of arginase can be controlled by adjusting the parameters affecting pegylation reaction, such as the ratio of protein/PEG reagent, reaction time, and temperature. For example, each arginase molecule can be controlled to be conjugated with about 4-13 PEG molecules, and preferably with 6-12 molecules.

In one aspect, the pegylated arginase of the present invention is formed by covenlently conjugating of the amine reactive PEG reagents with the &amino groups of the lysines on the surface of the arginase, such as the amino group at K191, K224, K89, K284, or the α-amino group at the N terminus, or further pegylated at the sites of K4, K33, K41, K75, K150, K155, K313, and K322. The number of PEG molecules conjugated with each molecule of arginase can be controlled to about 4-13 PEG molecules, preferably 6-12 molecules by adjusting the parameters affecting pegylation reaction, such as the ratio of protein/PEG reagent, reaction time or temperature.

In one aspect of the present invention, one of the three cysteines at positions 45, 168 and 303 of the amino acid sequence of SEQ ID NO:1 (for example, cysteine 45, cysteine 168 or cysteine 303) of the pegylated arginase is mutated to alanine, glycine, valine, leucine, isoleucine, methionine, phenylalanine, tryptophan or proline; and preferably, said cysteine is mutated to alanine, wherein each PEG molecule of said pegylated arginase has an average molecular weight of about 5K; and each arginase molecule of said pegylated arginase is conjugated with about 4-13 PEG molecules, and preferably with 6-12 molecules. In a further aspect of the present invention, said pegylation is carried out using methoxy polyethylene glycol-succinimidyl propionate 5000.

In one aspect of the present invention, cysteines at positions 168 and 303 of amino acid sequence of SEQ ID NO:1 of the pegylated arginase are independently mutated to alanine, glycine, valine, leucine, isoleucine, methionine, phenylalanine, tryptophan or proline; and preferably, said cysteines are mutated to alanine, wherein each PEG molecule of said pegylated arginase has an average molecular weight of about 5K, and each arginase molecule of said pegylated arginase is conjugated with about 4-13 PEG molecules, and preferably with 6-12 molecules. In a further aspect of the present invention, said pegylation is carried out using methoxy polyethylene glycol-succinimidyl propionate 5000.

In one aspect of the present invention, cysteines at positions 45 and 303 of amino acid sequence of SEQ ID NO:1 of the pegylated arginase are independently mutated to alanine, glycine, valine, leucine, isoleucine, methionine, phenylalanine, tryptophan or proline; and preferably, said cysteines are mutated to alanine, wherein each PEG molecule of pegylated arginase has an average molecular weight of about 5K, and each arginase molecule of pegylated argianse is conjugated with about 4-13 PEG molecules, and preferably with 6-12 molecules. In a further aspect of the present invention, said pegylation is carried out using methoxy polyethylene glycol-succinimidyl propionate 5000.

In one aspect of the present invention, cysteines at positions 45 and 168 of amino acid sequence of SEQ ID NO:1 of the pegylated arginase are independently mutated to alanine, glycine, valine, leucine, isoleucine, methionine, phenylalanine, tryptophan or proline; and preferably, said cysteines are mutated to alanine, wherein each PEG molecule of said pegylated argianse has an average molecular weight of about 5K, and each arginase molecule of said pegylated arginase is conjugated with about 4-13 PEG molecules, and preferably with 6-12 molecules. In a further aspect of the present invention, said pegylation is carried out using methoxy polyethylene glycol-succinimidyl propionate 5000.

In one aspect of the present invention, cysteine at position 45, 168 and 303 of amino acid sequence of SEQ ID NO:1 of the pegylated arginase is independently mutated to alanine, glycine, valine, leucine, isoleucine, methionine, phenylalanine, tryptophan or proline; and preferably, said cysteine is mutated to alanine, wherein each PEG molecule of said pegylated arginase has an average molecular weight of about 5K, and each arginase molecule of said pegylated arginase is conjugated with about 4-13 PEG molecules, and preferably with 6-12 molecules. In a further aspect of the present invention, said pegylation is carried out using methoxy polyethylene glycol-succinimidyl propionate 5000.

The pegylated arginase of the present invention is substantially homogeneous. Being substantially homogeneous means that the product contains substantially the pegylated arginase, but it may contain small amounts of unreacted (i.e. not pegylated) protein or polymeric pegylated arginase. The present invention provides pegylated arginase having a purity of more than 90%, preferably more than 95%, and most preferably more than 98%. In the present invention, the term "purity of pegylated arginase" means the percentage of the pegylated arginase (i.e., arginase covalently linked with PEG) in the total arginase (arginase covalently linked with PEG, arginase not covalently linked with PEG and polymeric pegylated arginase). Generally, the product needs further purification because it comprises arginase that is not covalently linked with PEG and arginase in the polymeric form. Commonly used means of purification technique are known in the art, including the cation exchange chromatography and Tangenital Flow Filtration.

The pegylated arginase of the present invention has a half-life of at least 0.5 day; preferably, said arginase has a half-life of at least 2.5 days; and more preferably, said arginase has a half-life of at least 3.5 days in the blood or serum. The half-life of the arginase can be measured with the known and commonly used method in the art. There is certain relationship between the data measured for the half-life of arginase in the blood or serum and the animal model used. The half-life data obtained in an animal with higher metabolic rate (e.g., rat) is generally shorter than that of with lower metabolic rate (e.g., human).

The present invention provides a method for preparing a pegylated arginase. The said pegylation is achieved by conjugation of PEG molecule with the amino acid residue of the arginase. In the pegylated arginase of the present invention, each arginase molecule is linked with PEG molecules to form the pegylated arginase.

In the present invention, site-directed pegylation is achieved by chemical modification, wherein said chemical modification is carried out by covalently conjugate the groups on the arginase with PEG reagents. Said chemical modification can be specific, that is, the PEG molecule only cojugates with specific amino acid residue of the arginase using reagents that bind with specific group.

The present invention also provides the application/use of the arginase or the pegylated arginase mentioned above or the pharmaceutical composition containing the same in treating an arginase-related disease. Said arginase related diseases known in the field include conditions/disease/disorders related with arginine level in the body of mammals. Such conditions/disease/disorders include hyperargininemia. Due to arginase deficiency, the arginine in the body of a subject can not be degraded into urea and participate the ornithine metabolism cycle, so that the blood arginine level can be 7 to 10 times higher than normal blood value, at the same time the arginine level in the cerebrospinal fluid and urine and urea excretion of creatinine are also increased. Moreover, said conditions/disease/disorders include arginine-dependent hyperplasia or tumor. By studying the effect on cell growth, it was found that upon remove of arginine, the normal cells in the cell cycle G0 phase would enter a resting state and remain viable for several weeks without significant damage; when the concentration of arginine returned to normal level, the cells would return to normal cell cycle. Cells in proliferation or tumors, however, would proceed past the 'R' point of the cell cycle G1 phase to enter S phase at the deprivation of arginine, and undergo apoptosis soon. The apoptosis of hyperplasia cells or tumor cells as a result of arginine deficiency is irreversible. Therefore, scientists began to consider treating hyperplasia or tumor by controlling the level of arginine in the body.

The present invention also provides a pharmaceutical composition, wherein the active ingredient of the said pharmaceutical composition of the present invention is the arginase or the pegylated arginase as described above. The formulation of said pharmaceutical composition can be in the form of solid, solutions, emulsions, dispersions, micelles, liposomes, wherein the formulation contains one or more of the human arginase or pegylated arginase of the present invention as active ingredient and admixed with organic or inorganic carrier or excipient suitable for parenteral applications. Furthermore, adjuvants, stabilizers, thickeners, coloring agents and perfumes can be included. One or more isolated and substantially pure human arginases or pegylated arginases of the present invention are comprised as active ingredient in a sufficient amount to produce the desired effect on the conditions or diseases. The pharmaceutical compositions may be formulated in forms suitable for oral administration, such as tablets, pills, lozenges, hydration or oil based suspensions, dispersed powders or granules, emulsions, hard or soft capsules, or syrups. Formulations for oral administration may be encapsulated in accordance with techniques known in the art to slow down the decomposition and absorption in the gastrointestinal tract, thereby providing sustained effects for a longer time. The formulation may also be a sterile injectable solution or suspension form. The said suspension can be prepared according to methods known in the art by using dispersing or wetting agents and suspending agents.

The pharmaceutical composition of the present invention can be further formulated into a solid, liquid, suspension, micelle or liposome form. In one aspect of the present invention, the pharmaceutical composition is formulated into an oral administration or injectable form.

BRIEF DESCRIPTION OF THE DRAWINGS

FIG. 1 shows the nucleotide sequence of wide type arginase I.

FIG. 2 shows SDS-polyacrylamide gel electrophoresis analysis of human arginase I under reducing condition.

FIG. 6 shows SDS-polyacrylamide gel electrophoresis analysis of purified mutant arginase I (rhArgI-A45/168 and rhArgI-A45/168/303) under reducing and non-reducing conditions.

FIG. 8 shows Mass Spectrometry analysis of pegylated arginase I.

DETAILED DESCRIPTION OF PREFERRED EMBODIMENTS OF THE INVENTION

Figure 3:
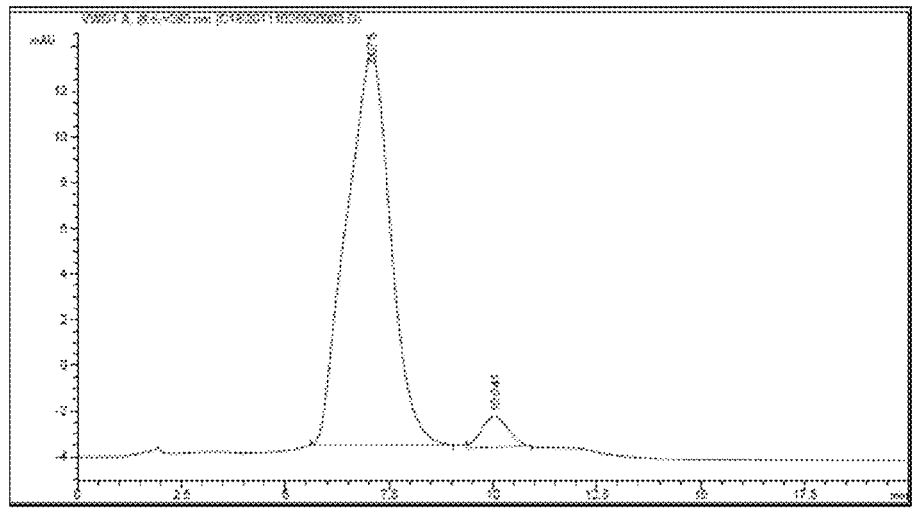
FIG. 3 shows the expression of human arginase by High Pressure Liquid Chromatography analysis.

This invention will be further illustrated using the embodiments described below. It should be understood that although these embodiments illustrate the preferred embodiments of the present invention, they are only given by ways of illustrated examples. With reference to the above description and embodiments, the skilled in the art can determine the essential characteristics of the invention, change and modify the invention in various ways in adaptation to other uses and conditions without deviating from the spirit and scope of the invention. Therefore, other than those shown and described herein, according to the foregoing any changes/modifications made to this invention will be apparent to the skilled in the art and these modifications are also intended to form part of the scope of the appended claims.

Example 1

Expression and Construction of His-Tag-Free Recombinant Human Arginse I Plasmid pET30a (+)-Rharginase-V Human arginase I gene sequence was published in 1987 (Haraguchi. Y. et al., 1987, Proc. Natl. Acad. Sci, 84, 412-415). Human arginase gene was amplified by Polymerase Chain Reacion (PCR) using human liver 5' stretch plus cDNA library (clontech) as template and primers ARG-V (+) and ARG-V (−) designed according to the aforesaid arginase I sequence. Primer ARG-V (+) contains an NdeI restriction endonuclease site, and ARG-V (−) primer contains a XhoI restriction endonuclease site. Using common laboratory techniques of molecular biology, human arginase I PCR product was obtained and confirmed by argarose gel electrophoresis. The above amplified human arginase I PCR product and commercially available expression vector pET30a (+) were digested with restriction endonucleases, NdeI and XhoI (Promega) separately at 37° C. for 1.5 h. The digested fragments were ligated overnight at 16° C. by T4 DNA ligase, and the resulting ligated recombinant plasmid was transformed into DH5α E. coli competent cells. The transformed cells were selected by plating and culturing on a kanamycin (30 μg/ml) containing LB agar plate. Plasmids containing the correct insert were identified by restriction endonuclease digest assay. The correct recombinant human arginase I expression plasmid, hereafter known as pET30a (+)-rharginase-V, was analyzed by sequencing to ensure the correct sequence and insertion of human arginase I gene. The insert size is 969 base pair in length. As shown in FIG. 1, it has a nucleotide sequence of SEQ ID No. 2.

```
ARG-V(+):
5' GGAATTCCATATGAGCGCCAAGTCCAGAACCATAG 3'
         NdeI

ARG-V(-):
5' CCGCTCGAGTTATTACTTAGGTGGGTTAAGGTAGTCAATAGG 3'
      XhoI
```

Example 2

Expression of His-Tag-Free Recombinant Human Arginase I Plasmid DNA pET30a (+)-Rharginase-V and Purification of Target Protein One-hundred μl of competent BL21(DE3) cells were thawed on ice. One μl of pET30a (+)-V recombinant plasmid was added to the competent cells and incubated on ice for 30 min. The mixture was then heat shock treated in a 42° C. water bath for 90 s followed by a further incubation on ice for 2 min. Five-hundred μl of LB broth was added to the transformed cells and shake-cultured at 37° C., 150 rpm for 1 h. After incubation, 2000 of the transformed cell suspension was plated and spread on a kanamycin LB agar plate, which is then incubated upside-down in a 37° C. incubator for 16 h.

Single colony transformed with recombinant plasmid was selected, transferred into 25 ml of LB broth and shake-cultured at 37° C., 150 rpm until the optical density 600 nm (OD600 nm) reaching 0.6-0.8. A final concentration of 0.2 mM IPTG was added to the culture to induce target protein expression for 3 h. Target protein expression of the selected clones was analyzed using SDS-polyacrylamide gel electrophoresis (SDS-PAGE). The clones with the higher protein expression were stored in glycerol stock as engineered bacteria.

The engineered bacteria cells were fed-batch cultured in a 15 L fermentor. When OD600 nm reaches 12-13, a final concentration of 0.2 mM IPTG was added into the culture to induce target protein expression for 3-4 h. Induced bacteria cells were collected and lysed. The cell lysate was centrifuged and the supernatant was collected for subsequent target protein separation and purification.

Target protein purification was performed using CM cation liquid chromatography. Tris-HCl was used to equibrate the column prior to sample loading. The lysate supernatant of bacterial cell was loaded into the column, followed by washing with three column volumes of equilibration buffer to remove weakly associated or non-specifically bound impurities. When the reading of UV280 nm stabilized, the target protein was eluted using an elution buffer containing Tris-HCl and NaCl. The protein peaks eluted from the column were collected and analyzed by SDS-PAGE and High Pressure Liquid Chromatography (HPLC).

Experimental results were illustrated in FIGS. 2 and 3.

FIG. 2 shows the result of SDS-PAGE analysis of human arginase I expression level. The samples in each lane are as follow:

1. protein molecular weight standard; 2. bacterial lysate supernatant; 3. purified His-tag-free human arginase I; 4. CM cation exchange column flow through.

FIG. 3 shows the result of the HPLC analysis of purified human argianse I.

As shown in FIGS. 2 and 3, the purity of arginase obtained via the above chromatography procedure is more than 90%.

Examples 3

Site-Directed Mutagenesis of Human Arginase I (rhArgI)

Site-directed mutations were introduced at positions 45, 168 and 303 of amino acid sequence of human arginase I using QuickChange site-directed mutagenesis kit (Stratagene). Recombinant plasmid pET30a-rharginase I-V containing wild type human arginase was used as template. Codons that encode for cysteine (TGT) at positions 45, 168 and 303 were independently mutated to codons that encode for alanine (GCT), resulting in single, double or triple-site mutations. The primers intended to introduce the replacement codon GCT at positions 45, 168, and 303 of human arginase I are shown as below:

```
ARG-m45(+):
5' GAGAAACTTAAAGAACAAGAGGCTGATGTGAAGGATTATGGGG 3'

ARG-m45(-):
5' CCCCATAATCCTTCACATCAGCCTCTTGTTCTTTAAGTTTCTC 3'

ARG-m168(+):
5' GATTCTCCTGGGTGACTCCCGCTATATCTGCCAAGGATATTG 3'

ARG-m168(-):
5' CAATATCCTTGGCAGATATAGCGGGAGTCACCCAGGAGAATC 3'

ARG-m303(+):
5' GTTGCAATAACCTTGGCTGCTTTCGGACTTGCTCGGG 3'

ARG-m303(-):
5' CCCGAGCAAGTCCGAAAGCAGCCAAGGTTATTGCAAC 3'
```

PCR was conducted in accordance with the instruction provided in the mutagenesis kit. Non-mutated parental DNA template was digested with restriction endonuclease DpnI. The mutated plasmids were then transformed into competent cells and confirmed by sequencing. Clones that were transformed with the mutant arginase plasmid containing the mutation of cysteine encoding codon (TGT) to alanine encoding codon (GCT) were selected and expanded in LB broth culture. Target mutant plasmids were isolated using Wizard Plus mini prep kit.

Mutant human arginase I with single cysteine to alanine mutation at amino acid position 303, 168 or 45 was represented as rhArgI-A303, rhArgI-A168 or rhArgI-A45 respectively. Mutant human arginase I with double cysteine to alanine mutations at amino acid positions 168 and 303, at amino acid positions 45 and 303 and at amino acid positions 45 and 168 were represented as rhArgI-A168/303, rhArgI-A45/303 and rhArgI-A45/168 respectively. Mutant human arginase I with three cysteine to alanine mutations at amino acid positions 45, 168 and 303 was represented as rhArgI-A45/168/303. Plasmids containing the above arginase mutant inserts were represented as pET30a(+)-rhArgI-A303, pET30a(+)-rhArgI-A168, pET30a(+)-rhArgI-A45, pET30a(+)-rhArgI-A168/303, pET30a(+)-rhArgI-A45/303, pET30a(+)-rhArgI-A45/168 or pET30a(+)-rhArgI-A45/168/303.

One-hundred μl of competent BL21(DE3) cells were thawed on ice. One pi of the mutant construct was added to the BL21(DE3) competent cells and incubated on ice for 30 min. The mixture was then heat shock treated at 42° C. for 90 s, followed by a further incubation on ice for 2 min. Five-hundred pi of LB broth was added to the transformed cells and shake-cultured at 37° C., 150 rpm for 1 h. After incubation, 2000 of the transformed cell suspension was plated and spread on a kanamycin LB agar plate and incubated upside-down at 37° C. for 16 h.

Single colony transformed with recombinant plasmid was selected, transferred into 25 ml of LB broth, and shake-cultured at 37° C., 150 rpm, until the optical density at 600 nm (OD600 nm) reaching 0.6-0.8. A final concentration of 0.2 mM IPTG was added to the culture to induce target protein expression for 3 h. Target protein expression in the selected clones was analyzed using SDS-PAGE. The clones with higher protein expression were stored in glycerol stock as engineered bacteria.

Example 4

Expression and Protein Purification of Site-Specific Mutated Arginase I

Engineered *E. coli* cells transformed with mutant arginase I (rhArgI) plasmids (pET30a(+)-rhArgI-A303, pET30a(+)-rhArgI-A168, pET30a(+)-rhArgI-A45, pET30a(+)-rhArgI-A168/303, pET30a(+)-rhArgI-A45/303, pET30a(+)-rhArgI-A45/168 or pET30a(+)-rhArgI-A45/168/303) were fed-batch cultured in a 15 L fermentor. When OD600 nm reached 12-13, a final concentration of 0.2 mM IPTG was added to the culture to induce target protein expression for 3-4 h. The bacterial cells were collected and lysed. The cell lysate was centrifuged and the supernatant was collected for sebsequent protein isolation and purification.

Target protein purification was performed using CM cation exchange column. Tris-HCl was used to equilibrate the column prior to sample loading. The lysate supernatant of bacterial cells was loaded into the column, followed by washing with three times column volume of equilibration buffer to remove weakly associated or non-specifically bound impurities. When the reading of UV 280 nm stabilized, target protein was eluted using an elution buffer containing Tris-HCl and NaCl. The protein peaks eluted from the column were collected to obtain mutant arginase I rhArgI-A303, rhArgI-A168, rhArgI-A45, rhArgI-A168/303, rhArgI-A45/303, rhArgI-A45/168 and rhArgI-A45/168/303.

Purity of the collected protein sample was analyzed by SDS-PAGE and HPLC. Using the above chromatography procedure, the purity of arginase was determined to be more than 90%.

Example 5

Activity of Site-Specific Mutant Arginase I (rhArgI)

The activity of arginase was determined by a spectrophotometric assay coupled with urease and glutamate dehydrogenase, which is shown by schematic diagram below. NADPH has optimal absorbance at the wavelength of 340 nm. When NADPH is oxidised to NADP+, the absorbance at 340 nm decrease. The activity of arginase can be correlated and determined by monitoring the decrease in absorbance at 340 nm together with the molar extinction coefficient of NADPH ($\Delta E340=6220\ M^{-1}\ cm^{-1}$).

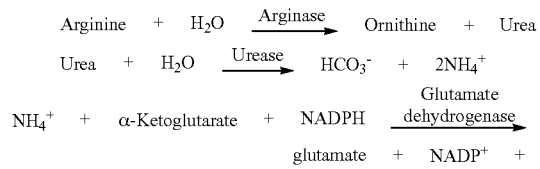

One Unit (U) of arginase activity was defined as the release of 1 µmol urea under the condition of 30° C., pH 8.3.

Specific activity of arginase was calculated using the following equation:

$$\text{Specific activity (U/mg)} = [(\Delta A/\Delta t) \times (1/\epsilon) \times 10^6 \times (1/2)] / [E]$$

$\Delta A$=Differences in absorbance at 340 nm
$\epsilon$=NADPH Michaelis-Menten constant(Km) (6220 $M^{-1}cm^{-1}$)
[E]=enzyme concentration in the reaction mixture (mg/mL)

Using the above assay, the specific activity of various mutant arginase I (rhArgI-A303, rhArgI-A168/303, rhArgI-A45/303, rhArgI-A45/168 and rhArgI-A45/168/303) were determined to be 747±63 U/mg, 814±91 U/mg, 786±58 U/mg, 782±19 U/mg, and 759±68 U/mg respectively. The specific activity of wild type human arginase I was determined to be 491±42 U/mg, demonstrating a significant increase of arginase activity after the non-polar nonioinic amino acid cysteines at positions 168/303, 45/303, 45/168 and 45/168/303 were mutated to non-polar amino acid alanines.

Example 6

SDS-PAGE Analysis of Wild Type and Mutant Arginase I (rhArgI)

The polyacrylamide gel was prepared using traditional method. Samples were treated under reducing (i.e. β-mecaptoethanol was included in the sample loading buffer to destroy inter and intra molecular disulfide bonds) or non-reducing condition prior to analysis to decipher the intramolecular disulfide bridge formation of wild type and various mutant arginse I using 12% polyacrylamide gel electrophoresis (FIG. 4, 5, 6A, 6B).

Figure 4:
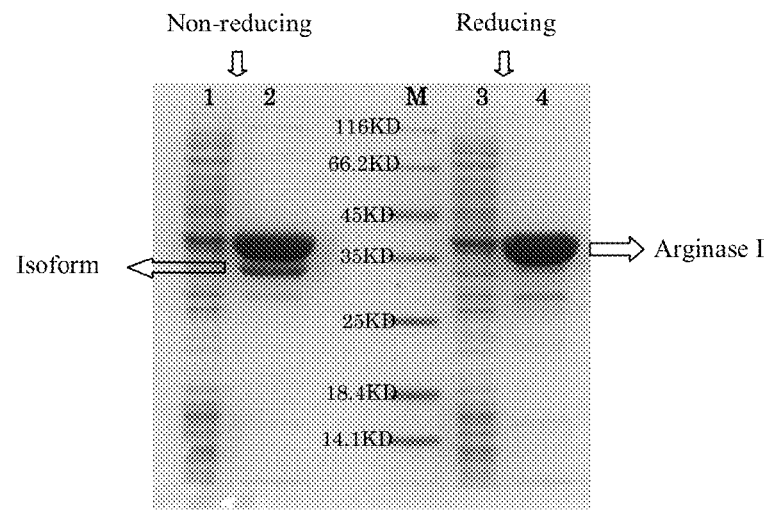
FIG. 4 shows the test results of wild type and mutant arginase I with reducing and non-reducing SDS-polyacrylamide gel electrophresis.

FIG. 4 shows the results of the SDS-PAGE analysis of wild type arginase I after treatment under reducing and non-reducing conditions. The samples in the lanes are as follow: Lane 1 and 3: bacterial cell lysate supernatant; Lane 2: purified His-tag-free arginase (non-reducing); M: protein molecular weight standard; Lane 4: purified His-tag-free human arginase I (reducing).

Figure 5:
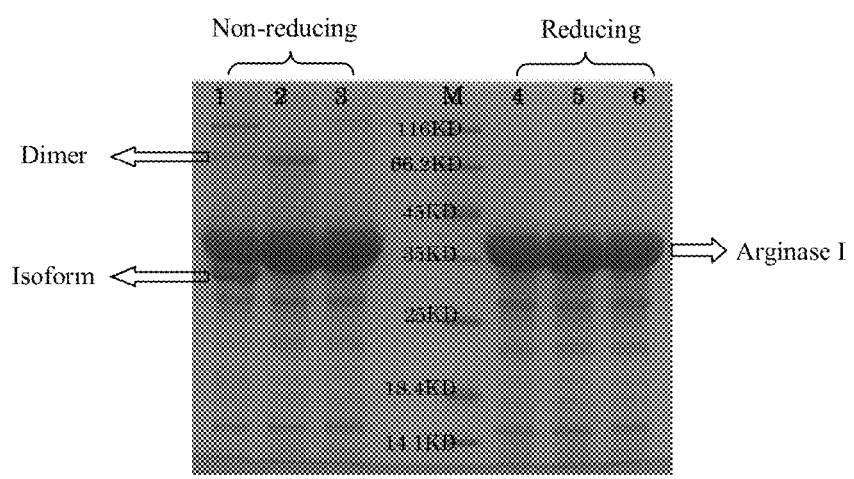
FIG. 5 shows SDS-polyacrylamide gel electrophoresis analysis of purified mutant arginase I (rhArgI-A303, rhArgI-A168/303 and rhArgI-A45/303) under reducing and non-reducing conditions.

FIG. 5 shows the results of the SDS-PAGE analysis of purified mutant arginase I (rhArgI-A303, rhArgI-A168/303 and rhArgI-A45/303) under reducing and non-reducing conditions. The samples in each lane are as follow: Lane 1: mutant arginase I, rhArgI-A303 (non-reducing); Lane 2: mutant arginase I, rhArgI-A168/303 (non-reducing); Lane 3: mutant arginase I, rhArgI-A45/303 (non-reducing); M: protein molecular weight standard; Lane 4: mutant arginase I, rhArgI-A303 (reducing); Lane 5: mutant arginase I, rhArgI-A168/303 (reducing); Lane 6: mutant arginase I, rhArgI-A45/303 (reducing).

Figure 6A:
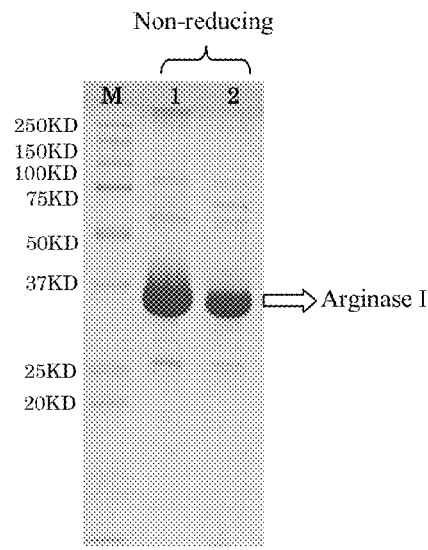
FIG. 6a shows non-reducing SDS-polyacrylamide gel electrophoresis analysis of purified mutant arginase I (rhArgI-A45/168 and rhArgI-A45/168/303).

FIG. 6a shows the results of the SDS-PAGE analysis of purified mutant arginase I (rhArgI-A45/168 and rhArgI-A45/168/303) under non-reducing condition. The samples in each lane are as follow: M: protein molecular weight standard; Lane 1: mutant arginase I, rhArgI-A45/168/303; Lane 2: mutant arginase I, rhArgI-A45/168.

Figure 6B:
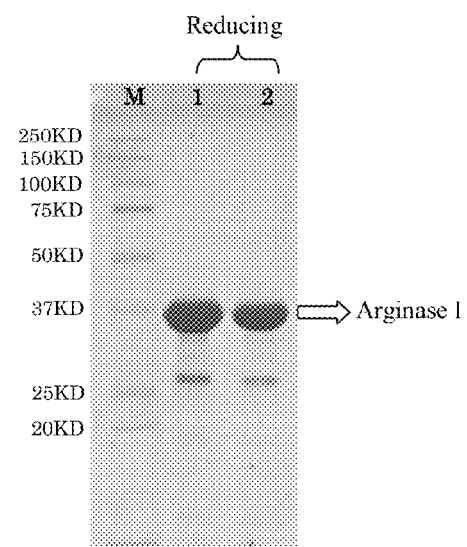
FIG. 6b shows reducing SDS-polyacrylamide gel electrophoresis analysis of purified mutant arginase I (rhArgI-A45/168 and rhArgI-A45/168/303).

FIG. 6b shows the results of the SDS-PAGE analysis of purified mutant arginase I (rhArgI-A45/168 and rhArgI-A45/168/303) under reducing condition. The samples in each lane are as follow: M: protein molecular weight standard; Lane 1: mutant arginase I, rhArgI-A45/168/303; Lane 2: mutant arginase I, rhArgI-A45/168.

As revealed from the SDS-PAGE analysis of arginase I under reducing and non-reducing conditions, wild type human arginase I have other conformations under the stated experimental conditions of this invention. Under such condition, when cysteine at position 303 was mutated to alanine, other conformations were also present. However, when either two (rhArgI-A168/303, rhArgI-A45/303, or rhArgI-A45/168) or all of the three cysteine residues at amino acid positions 45, 168 and 303 were mutated to alanine, only one conformation was detected under non-reducing condition (FIG. 5 and FIG. 6A). Not limited by any known theories, the inventor believes the presence of multiple conformations for wild type human arginase I at non-reducing SDS-PAGE is probably due to intramolecular disulfide bond formation that is contributed by cysteines 45, 168 and 303 under certain conditions. When only cysteine 303 was mutated to alanine, such conformation of arginase I mutant could also be detected by SDS-PAGE under non-reducing condition possibly due to the formation of intramolecular disulfide bonds between unmutated cysteines 45 and 168. When either two or all of the three cysteine residues at positions 45, 168 and 303 were mutated (rhArgI-A168/303, rhArgI-A45/303, rhArgI-A45/168 or rhArgI-A45/168/303) all possibilities of disulfide bond formation will be abolished, resulting in only one conformation being detected in the SDS-PAGE analysis.

Example 7

Pegylatoin of Mutant Arginase I (rhArgI) and Purification of Pegylated Protein (1) Pegylation Using Methoxy Polyethylene Glycol Maleimide (mPEG-MAL 40000).

Site-specific mutants of arginase I (rhArgI-A303/168 or rhArgI-A45/303) were mixed separately with methoxy polydthylene glycol maleimide in a molar ratio range of 1:5-1:10 in 20 mM PBS buffer (pH 7.0). Said methoxy polyethylene glycol maleimide was Y-shape branched, consisting of two polyethylene glycol chains with a molecular weight of 40 kDa. The pegylatoin reaction was carried out at room temperature for 2-4 h. At the end of the reaction, the end products were stored in a 4° C. refrigerator.

Site-specific pegylated human arginase I was isolated and purified using Macro SP matrix cation exchange column to remove residual unreacted proteins and PEGs. Phosphate buffer and NaCl (1M) containing phosphate buffer were used as equilibration and elution buffer respectively. Prior to sample loading, pegylated protein samples were diluted with distilled water until the sample electric conductivity is identical to that of the equilibration buffer; and column was equilibrated with five times column volume of equilibration buffer. After sample loading, the column was further washed with five times column volume of equilibration buffer and eluted with 35% elution buffer. The eluant containing protein peaks were collected and desalted using G25 column. Target proteins were collected and analyzed by SDS-PAGE.

(2) Pegylatoin of Protein Using Methoxy Polyethylene Glycol Succinimidyl Propionate (mPEG-SPA 5000) and Purification of Pegylated Protein.

Pegylation modification of wild type and various site specific mutated arginase I (rhArgI-A303/168, rhArgI-A303/45, rhArgI-A45/168, and rhArgI-A45/168/303) was conducted. The reaction conditions were as follows: wild type or various site specific mutated arginase I, at the protein concentration of 8 mg/ml, was mixed separately with methoxy polyethylene glycol succinimidyl propionate (mPEG-SPA 5000) at the molar ratio range of 1:20-1:30 in 20 mM PBS buffer (pH 8.5-9.0) for 2 h at room temperature. The end products were stored in a 4° C. refrigerator.

The above pegylated products were purified by ultrafiltration with 100 KDa ultrafiltration membrane to remove unreacted methoxy poly(ethylene glycol) succinimidyl propionate. The pegylation products were mixed with 10 mM PBS buffer (pH 7.5) in a 1:1 volume ratio and ultrafiltrated to original volume. The process was repeated 15 times and target proteins were collected and analyzed by electrophoresis.

(3) SDS-PAGE and Enzymatic Activity Analysis of Pegylated Human Arginase I

The purified mPEG-MAL-40K pegylated arginase I and mPEG-SPA-5K pegylated arginase I were resolved and analysed by 8% SDS-PAGE.

Figure 7:
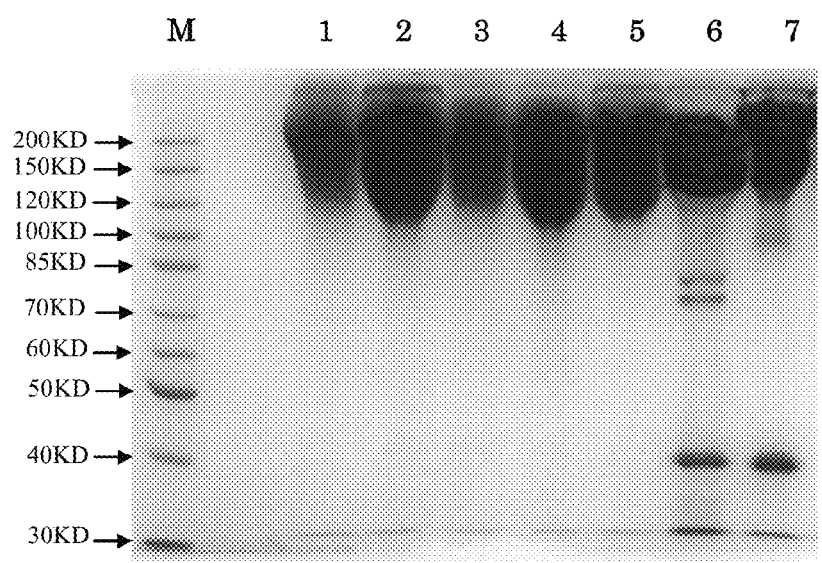
FIG. 7 shows non-reducing SDS-polyacrylamide gel electrophoresis analysis of pegylated human arginase I.

The results are shown in FIG. 7

FIG. 7: SDS-PAGE analysis of pegylated arginase I. The samples in each lane are as follow:

M: Protein molecular weight standard

RP-V-J5K: Recombinant wild type arginase I was reacted with methoxy polyethylene glycol succinimidyl propionate (mPEG-SPA 5000). The pegylated human arginase I (RP-V-J5K) was purified using 100 kDa ultrafiltration membrane and the purity is more than 95%;

RP-M2-J5K: Site-specific mutated arginase I (rhArgI-A168/303) was reacted with methoxy polyethylene glycol succinimidyl propionate (mPEG-SPA 5000). The pegylated human arginase I (RP-M2-J5K) was purified using 100 kDa ultrafiltration membrane and the purity is more than 95%;

RP-M3-J5K: Site-specific mutated arginase I (rhArgI-A45/303) was reacted with methoxy polyethylene glycol succinimidyl propionate (mPEG-SPA 5000). The pegylated human arginase I (RP-M3-J5K) was purified using 100 kDa ultrafiltration membrane and the purity is more than 95%;

RP-M4-J5K: Site-specific mutated arginase I (rhArgI-A45/168/303) was reacted with methoxy polyethylene glycol succinimidyl propionate (mPEG-SPA 5000). The pegylated human arginase I (RP-M4-J5K) was purified using 100 kDa ultrafiltration membrane and the purity is more than 95%;

RP-M7-J5K: Site-specific mutated arginase I (rhArgI-A45/168) was reacted with methoxy polyethylene glycol succinimidyl propionate (mPEG-SPA 5000). The pegylated human arginase I (RP-M7-J5K) was purified using 100 kDa ultrafiltration membrane and the purity is more than 95%;

A168/303-Y40K: Site-specific mutated arginase I (rhArgI-A168/303) was reacted with Y-shape branched polyethylene glycol maleimide 40K (Y-MAL-40K). Pegylated human arginase I was purified by Macrocap SP matrix cation exchange column. The pegylated arginase I protein conjugated with one PEG chain Y-MAL-40K at cysteine 45 (A168/303-Y40K) accounts more than 85% of the total reaction products.

A45/303-Y40K: Site-specific mutated arginase I (rhArgI-A45/303) was reacted with Y-shape branched polyethylene glycol maleimide 40K (Y-MAL-40K). Pegylated human arginase I was purified by Macrocap SP matrix cation exchange column. The pegylated arginase I protein conjugated with one PEG chain Y-MAL-40K at cysteine 168 (A45/303-Y40K) accounts for more than 85% of the total reaction products.

Using the coupled spectrophotometric assay previously described, the activity of different pegylated human arginase I was measured and determined by changes in absorbance of NADPH. Test results showed that the pegylated products preserved the arginase activity, wherein the specific activities of A168/303-Y40K and A45/303-Y40K were 551±68 U/mg and 595±41 U/mg respectively, while the specific activities of RP-M2-J5K, RP-M3-J5K, RP-M4-J5K and RP-M7-J5K were 726±66 U/mg, 747±72 U/mg, 712±69 U/mg, and 838±8 U/mg respectively. The specific activity of pegylated wild type human arginase I (RP-V-J5K) was determined to be 537±55 U/mg.

(4) Molecular Mass Distribution Analysis of Pegylated Human Arginase I.

Human arginase I pegylated at different sites using different pegylatoin methods were analyzed by matrix-assisted laser desorption/ionization time of flight Mass Spectrometry (MALDI-TOF-MS) to determine the molecular mass distribution of the test samples. All experiments were performed on a Bruker Daltonics Autoflex™ TOF/TOF system based on time-of flight and equipped with a nitrogen laser to desorb and ionize the samples. The instrument was operated in the positive-ion linear mode with an accelerating potential of +20 kV.

Figure 8A:
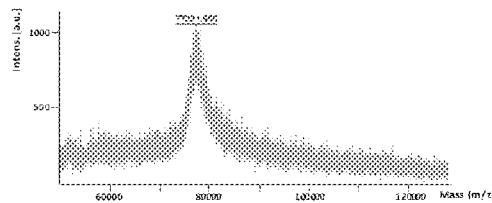
FIG. 8a shows Mass Spectrometry analysis of pegylated arginase I: A168/303-Y40K.
Figure 8B:
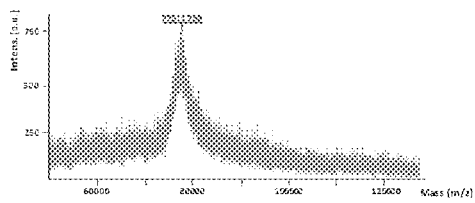
FIG. 8b shows Mass Spectrometry analysis of pegylated arginase I: A45/303-Y40K.
Figure 8C:
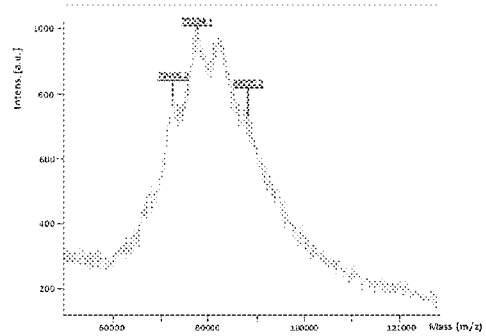
FIG. 8c shows Mass Spectrometry analysis of pegylated arginase I: RP-V-J5K.
Figure 8D:
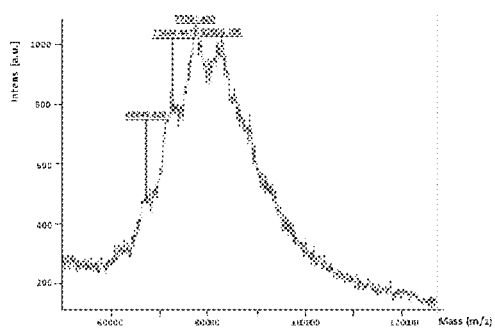
FIG. 8d shows Mass Spectrometry analysis of pegylated arginase I: RP-M2-J5K.
Figure 8E:
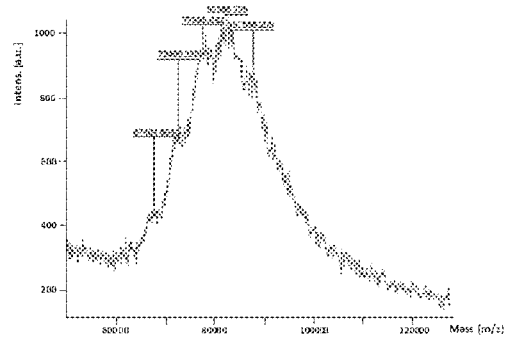
FIG. 8e shows Mass Spectrometry analysis of pegylated arginase I: RP-M3-J5K.
Figure 8F:
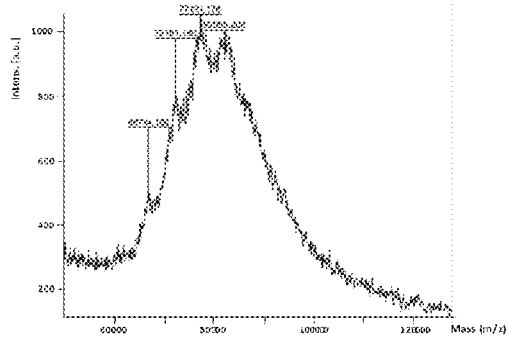
FIG. 8f shows Mass Spectrometry analysis of pegylated arginase I: RP-M4-J5K.
Figure 8G:
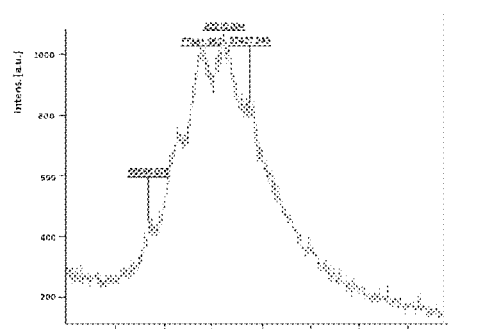
FIG. 8g shows Mass Spectrometry analysis of pegylated arginase I: RP-M7-J5K.
Figure 9:
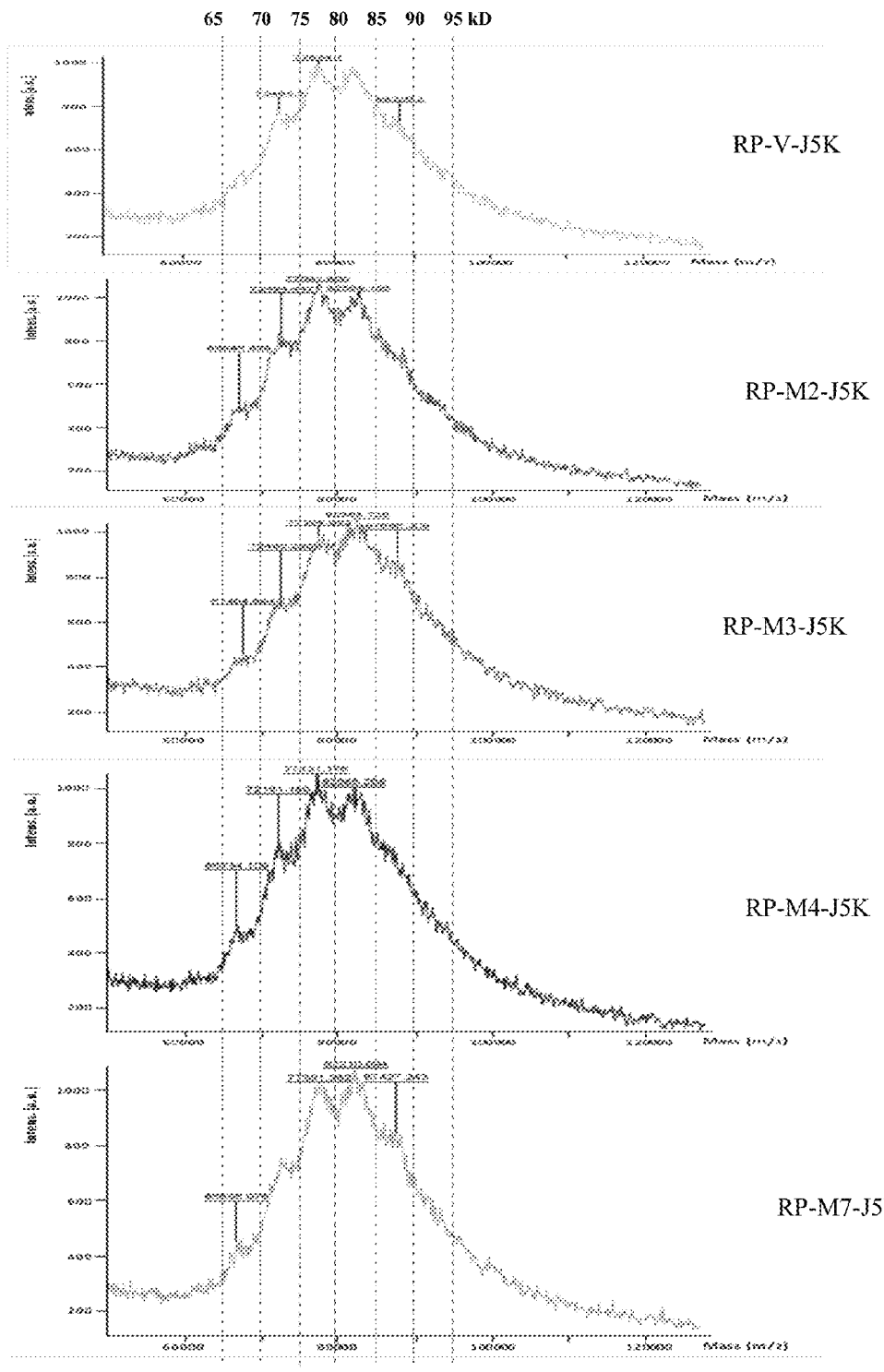
FIG. 9 shows the consolidated figures of Mass Spectrometry analysis of pegylated arginase.

Experimental results were shown in FIGS. 8 and 9.

FIG. 8a shows the results of the Mass Spectrometry analysis of pegylated arginase I, A168/303-Y40K, showing the molecular weight of A168/303-Y40K to be approximately 77 kDa.

FIG. 8b shows the results of the Mass Spectrometry analysis of pegylated arginase I, A45/303-Y40K, showing the molecular weight of A45/303-Y40K to be approximately 77 kDa.

FIG. 8c shows the results of the Mass Spectrometry analysis of pegylated arginase I, RP-V-J5K.

FIG. 8d shows the results of the Mass Spectrometry analysis of pegylated arginase I, RP-M2-J5K.

FIG. 8e shows the results of the Mass Spectrometry analysis of pegylated arginase I, RP-M3-J5K.

FIG. 8f shows the results of the Mass Spectrometry analysis of pegylated arginase I, RP-M4-J5K.

FIG. 8g shows the results of the Mass Spectrometry analysis of pegylated arginase I, RP-M7-J5K.

FIG. 9 shows the consolidated figures of pegylated arginase I, RP-V-J5K, RP-M2-J5K, RP-M3-J5K, RP-M4-J5K, and RP-M7-J5K, showing that pegylatoin of arginase I using mPEG-SPA 5000 produces products with molecular range between 65 and 95 kDa, i.e. every arginase I molecule conjugated with 6-12 PEG molecules, each with a molecular weight of 5000.

Example 8

In-Vivo Pharmacokinetic and Pharmacodynamics Analysis of Site Specific Pegylated Human Arginase I Pharmacokinetics and pharmacodynamics profiles of different pegylated human arginase I were evaluated after single intravenous administration to Sprague Dawley rats at a dosage of 3 mg/kg. These studies were conducted by Pharmalegacy Laboratories Limited (Shanghai). Blood samples were collected pre-dose, 2 min, 1 h, 4 h, 24 h, 72 h, 120 h, 168 h and 240 h after dosing for serum arginase and arginine analysis. Approximately 0.4 mL of blood samples were collected at each time-point from orbital vein after anesthesia by isoflurane and transferred to a 2-mL centrifuge tube. Samples were placed at room temperature for 30 min until centrifugation at 4,000 g for 15 min at 4° C.

Serum concentrations of arginase I were determined by a quantitative sandwich enzyme immunoassay with kits provided by Shanghai ExCell Biology, Inc. Anti-human arginase I monoclonal antibody was coated on the surface of the wells of the ELISA plate. Samples or protein standards of human arginase I were added separately into the wells of the ELISA plate (1000 µl/well), which was then covered with sealer tape and incubated at 37° C. for 90 min to allow immunocomplex formation between monoclonal antibody and human arginase I. After incubation, the plate was washed five times and rabbit anti-human arginase I polyclonal antibodies (1000 well) was added to the wells. It was covered with sealer tape again and further incubated at 37° C. for 60 min. After the second incubation, the plate was washed again for five times, HRP-conjugated goat anti-rabbit IgG (1000 well) was added to each well and co-incubated for 30 min. After another five times washing, chromogenic substrate was added into the wells and incubatied in the dark for 10-15 min. Stop solution was added to each well and mixed well. The optical density at 450 nm was measured within 10 min after adding the stop solution. The standard curve was generated using quadratic fit method for regression equation and the arginase I concentration of each samples was calculated using the measured OD value. The PK parameters were derived using WinnoLin with a non-compartmental assay method. The half-life ($T_{1/2}$) values of various forms of site-specific pegylated human arginase I, A168/303-Y40K, A45/303-Y40K, RP-M2-J5K, RP-M3-J5K, RP-M4-J5K and RP-M7-J5K were determined to be 27.2±3.8 h, 15.1±0.6 h, 40.7±13.2 h, 53.5±14.2 h, 59.5±9.9 h, and 50.5±13.0 h respectively. The half-life ($T_{1/2}$) of pegylated wild type human arginase I, RP-V-J5K, was determined to be 43.8±4.4 h.

TABLE 1

The pharmacokinetic parameters (average ± standard deviation; n = 6) of single dose administration of pegylated human arginase I in rat.

|  | $T_{1/2}$ (h) | $C_{max}$ (µg/mL) | $AUC_{last}$ (h * µg/mL) | $AUC_{INF}$ (h * µg/mL) |
| --- | --- | --- | --- | --- |
| A168/303-Y40K | 27.2 ± 3.8 | 45.2 ± 5.1 | 2077.5 ± 160.6 | 2083.9 ± 163.3 |
| A45/303-Y40K | 15.1 ± 0.6 | 105.2 ± 66.9 | 548.1 ± 50.3 | 564.5 ± 50.8 |
| RP-V-J5K | 43.8 ± 4.4 | 42.2 ± 3.6 | 1918.7 ± 271.0 | 2687.0 ± 290.2 |
| RP-M2-J5K | 40.7 ± 13.2 | 36.0 ± 6.0 | 1585.0 ± 184.8 | 2505.6 ± 534.8 |
| RP-M3-J5K | 53.5 ± 14.2 | 34.4 ± 7.4 | 2675.3 ± 560.4 | 3577.4 ± 865.8 |
| RP-M4-J5K | 59.5 ± 9.9 | 34.7 ± 8.7 | 2265.7 ± 659.8 | 3147.8 ± 673.0 |
| RP-M7-J5K | 50.5 ± 13.0 | 56.5 ± 11.0 | 4574.6 ± 1268.2 | 4939.5 ± 1308.1 |

Serum arginine concentration was measured using HPLC-Mass Spectrometry (Agilent 1200 HPLC coupled with API 4000 triple-quadrupole MS). An aliquot of rat serum was diluted with 4900 of deionized water. Acetonitrile (3800) was added and mixed with 200 of diluted serum sample. The mixture was centrifuged at 14,000 rpm for 14 mins and the supernatant was loaded and analyzed by LC-MS/MS. The HPLC was performed using Venusil HILIC/VH951002-0 column with 0.1% TFA as mobile phase A and 95% acetonitrile as mobile phase B at a flow rate of 0.3 ml/min. Serum arginine levels were determined before dosing and 2 min, 1 h, 4 h, 24 h, 72 h, 120 h, 168 h and 240 h after dosing. Results showed that serum arginine levels in all test animals were dropped to a concentration below detection limit (0.5 µg/ml) within a very short time frame (5 min) and maintained a sustainable low arginine level for certain time, although the test articles were pegylated in different manners. After that, serum arginine level gradually increased, but at different rates. Compared to the study groups treated with RP-M2-J5K, RP-M3-J5K, RP-M4-J5K, or RP-M7-J5K, serum arginine level rised faster in the study groups treated with 168/303-Y40K or A45/303-Y40K. At 72 h after dosing, the serum arginine level returned to 15%-20% of the pre-dose level in animals treated with single dose of 168/303-Y40K or A45/303-Y40K. At 120 h after dosing, the serum arginine level almost returned to the pre-dose level in animals treated with A45/303-Y40K. While the serum arginine level of animals treated with RP-M2-J5K, RP-M3-J5K, RP-M4-J5K or RP-M7-J5K could maintain a sustainable low level for a longer period of time. At 72 h after dosing, the serum arginine still maintained at a level lower than 5% of the pre-dose level.

This invention uses site-directed mutagenesis to mutate either one, or two or all of the three cysteine residues at positions 45, 168 and 303 of human arginase I to other amino acids, particularly, alanine, to obtain human arginase with higher specific activity. The human arginase in this invention does not contain any potentially immunogenic his-tag protein sequence. In addition, this invention provides a pegylated human arginase using amine-reactive poly(ethylene glycol) to modify the N-terminus α-NH2 or ε-NH2 of surface lysine. Such modification significantly increases its half-life in mammals, which can be as long as 40-60 h in sera of rats.

What is claimed is:

1. An arginase, wherein said arginase is human arginase I comprising an amino acid sequence of SEQ ID NO:1 comprising a mutation at position 45 of said SEQ ID NO:1; wherein said mutation is from cysteine to alanine; wherein said arginase has activity.

2. The arginase of claim 1, wherein said arginase further comprises a mutation at any one or two of positions 168 and 303 of SEQ ID NO:1.

3. The arginase of claim 1, wherein said arginase has an activity of at least about 500 U/mg.

4. A pegylated arginase comprising said arginase of claim 2, wherein said arginase is conjugated with polyethylene glycol (PEG) by pegylation modification.

5. The pegylated arginase of claim 4, wherein the total molecular weight of said PEG molecule conjugated with each molecule of said arginase is about 20-70K.

6. The pegylated arginase of claim 4, wherein said PEG molecule has an average molecular weight of about 2-40K.

7. The pegylated arginase of claim 4, wherein the pegylation is achieved by covalently conjugating a PEG molecule with a moiety of said arginase using a pegylation reagent; wherein said pegylation reagent comprises pegylation reagents conjugated with ε-NH$_2$ of surface lysine or N-terminal α-NH$_2$ of the protein and pegylation reagents conjugated with thiol group or carboxyl group of amino acids of the protein; wherein said pegylation reagent is selected from a group consisting of methoxy polyethylene glycol-succinimidyl propionate (mPEG-SPA), mPEG-succinimidyl butyrate (mPEG-SBA), mPEG-succinimidyl succinate (mPEG-SS), mPEG-succinimidyl carbonate (mPEG-SC), mPEG-succinimidyl glutarate (mPEG-SG), mPEG-N-hydroxyl-succinimide (mPEG-NHS), mPEG-tresylate and mPEG-aldehyde.

8. The pegylated arginase of claim 4, wherein any one of said cysteines at positions 168 and 303 of said SEQ ID NO:1 is mutated to alanine.

9. A pharmaceutical composition for treating an arginase-related disease comprising said pegylated arginase of claim 4.

10. A method for treating an arginase-related disease, comprising administrating said pegylated arginase of claim 4.

11. The arginase of claim 2, wherein any one of said cysteines at positions 45, 168 and 303 of said SEQ ID NO:1 is mutated to alanine.

12. The arginase of claim 2, wherein any two of said cysteines at positions 45, 168 and 303 of said SEQ ID NO:1 are mutated to alanine.

13. The arginase of claim 2, wherein all of said cysteines at positions 45, 168 and 303 of said SEQ ID NO:1 are mutated to alanine.

14. The pegylated arginase of claim 4, wherein any two of said cysteines at positions 45, 168 and 303 of said SEQ ID NO:1 are mutated to alanine.

15. The pegylated arginase of claim 4, wherein all of said cysteines at positions 45, 168 and 303 of said SEQ ID NO:1 are mutated to alanine.

16. The pegylated arginase of claim 4, wherein each of said arginase molecules is conjugated with about 4-13 PEG molecules.

17. The pegylated arginase of claim 16, wherein each of said arginase molecules is conjugated with about 6-12 PEG molecules.

18. The pegylated arginase of claim 4, wherein any two of said cysteines at positions 45, 168 and 303 of said SEQ ID NO:1 are mutated to alanine; said PEG molecule has an average molecular weight of about 5K; each of said arginase molecules is conjugated with about 6-12 PEG molecules.

19. The pegylated arginase of claim 4, wherein any one of said cysteines at positions 168 and 303 of said SEQ ID NO:1 is mutated to alanine; said PEG molecule has an average molecular weight of about 5K; each of said arginase molecules is conjugated with about 6-12 PEG molecules.

20. The pegylated arginase of claim 4, wherein the purity of said pegylated arginase is above 90%.

21. The pegylated arginase of claim 7, wherein said pegylation reagent is methoxy polyethylene glycol-succinimidyl propionate (m PEG-SPA).

22. The pharmaceutical composition of claim 9, wherein said disease is selected from hyperargininemia and arginine-dependent hyperplasia or tumor.

23. The method of claim 10, wherein said disease is selected from hyperargininemia and arginine-dependent hyperplasia or tumor.

* * * * *